(12) United States Patent
Cross, Jr. et al.

(10) Patent No.: US 8,108,051 B2
(45) Date of Patent: Jan. 31, 2012

(54) SURGICAL LEAD PADDLE

(75) Inventors: Thomas E. Cross, Jr., St. Francis, MN (US); Gabor Racz, Lubbox, TX (US)

(73) Assignee: Medtronic, Inc., Minneapolis, MN (US)

( * ) Notice: Subject to any disclaimer, the term of this patent is extended or adjusted under 35 U.S.C. 154(b) by 87 days.

(21) Appl. No.: 12/710,024

(22) Filed: Feb. 22, 2010

(65) Prior Publication Data

US 2010/0146783 A1 Jun. 17, 2010

Related U.S. Application Data

(63) Continuation of application No. 10/131,980, filed on Apr. 25, 2002, now Pat. No. 7,697,995.

(51) Int. Cl.
*A61N 1/00* (2006.01)

(52) U.S. Cl. .................................................. 607/117

(58) Field of Classification Search .................. 607/117
See application file for complete search history.

(56) References Cited

U.S. PATENT DOCUMENTS

| | | |
|---|---|---|
| 3,724,467 A | 4/1973 | Avery et al. |
| 4,077,398 A | 3/1978 | Ellis |
| 4,379,462 A | 4/1983 | Borkan et al. |
| 4,573,481 A | 3/1986 | Bullara |
| 4,607,644 A | 8/1986 | Pohndorf |
| 4,735,208 A * | 4/1988 | Wyler et al. .................. 600/377 |
| 4,903,702 A | 2/1990 | Putz |
| 4,920,979 A | 5/1990 | Bullara |
| 5,313,952 A | 5/1994 | Hoch |
| 5,391,200 A | 2/1995 | KenKnight et al. |
| 5,397,342 A | 3/1995 | Heil, Jr. et al. |
| 5,417,719 A | 5/1995 | Hull et al. |
| 5,505,201 A | 4/1996 | Grill, Jr. et al. |
| 5,643,330 A | 7/1997 | Holsheimer et al. |
| 5,689,877 A | 11/1997 | Grill, Jr. et al. |
| 5,702,429 A | 12/1997 | King |
| 5,913,882 A | 6/1999 | King |
| 5,964,702 A | 10/1999 | Grill, Jr. et al. |
| 6,052,608 A | 4/2000 | Young et al. |
| 6,064,905 A | 5/2000 | Webster, Jr. et al. |
| 6,066,165 A | 5/2000 | Racz |
| 6,161,047 A | 12/2000 | King et al. |
| 6,205,361 B1 | 3/2001 | Kuizma |
| 6,236,892 B1 | 5/2001 | Feler |
| 6,249,707 B1 | 6/2001 | Kohnen et al. |
| 6,292,702 B1 | 9/2001 | King et al. |

(Continued)

FOREIGN PATENT DOCUMENTS

WO 99/49933 10/1999

(Continued)

*Primary Examiner* — George Manuel
(74) *Attorney, Agent, or Firm* — Fredrikson & Byron, P.A.

(57) ABSTRACT

The present invention provides for an improved apparatus and method for electrical stimulation. A paddle having a thickness up to 0.030 inches is implanted adjacent the spinal cord dura mater to reduce the likelihood of paralysis due to stress on the spinal cord attributed to bulkier leads. The paddle is then positioned so that at least one of a plurality of electrodes is positioned over the area of the spinal cord requiring pain treatment; and then electric stimulation is applied to the electrodes to effect pain treatment. In another embodiment the paddle is curved about a vertical axis to substantially match the shape of a human spinal cord dura mater to help reduce lead migration.

19 Claims, 7 Drawing Sheets

U.S. PATENT DOCUMENTS

| | | |
|---|---|---|
| 6,309,401 B1 | 10/2001 | Redko et al. |
| 6,385,491 B1 | 5/2002 | Lindemans et al. |
| 6,415,187 B1 | 7/2002 | Kuzma et al. |
| 6,463,335 B1 | 10/2002 | Münch et al. |
| 6,522,932 B1 | 2/2003 | Kuzma et al. |
| 6,529,774 B1 | 3/2003 | Greene |
| 2002/0035388 A1 | 3/2002 | Lindemans et al. |
| 2002/0111661 A1 | 8/2002 | Cross et al. |
| 2003/0036787 A1 | 2/2003 | Redko et al. |

FOREIGN PATENT DOCUMENTS

| | | |
|---|---|---|
| WO | 99/56818 | 11/1999 |

* cited by examiner

SURGICAL LEAD PADDLE

PRIORITY CLAIM

This application is a continuation of U.S. patent application Ser. No. 10/131,980, filed Apr. 25, 2002, the disclosure of which is hereby incorporated by reference.

FIELD OF THE INVENTION

The present invention generally relates to the field of implantable medical devices, and more particularly to a medical electrical lead providing improved implantation capabilities.

BACKGROUND OF THE INVENTION

Electrical stimulation of electrically excitable tissue such as the brain and/or nerve tissue of the spinal cord or peripheral nerve can result in pain reduction and/or elimination for a living organism having the electrical stimulation performed. Thus, for example, medical leads having electrode contacts have been implanted near the spinal column of the human body to provide pain relief for chronic intractable pain. The nerve tissue within the spinal column is stimulated electrically to reduce pain sensations at other parts of the body.

Depending on the location of the pain sensation, and the particularities of each different human body, the parameters of the stimulation signals applied near the electrically excitable tissue are adjusted to optimize pain reduction or elimination. For example, the area of excitation within the spinal column and the intensity of excitation can be varied by corresponding adjustment of the parameters of the stimulation signals.

During acute trial stimulation, in order to vary the area of excitation, an array of electrodes may be implanted near the nerve tissue within the spinal column or peripheral nerve. Then, each of those electrodes can be configured to have a polarity such that the desired area of the nerve tissue within the spinal column is electrically stimulated. In addition, parameters of the respective stimulation signal applied on each of those implanted electrodes can be varied for a corresponding variation in the area of excitation within the spinal column and in the intensity of excitation at the pain site. Once the array of electrodes is implanted, a clinician who is knowledgeable of the effects of electrical stimulation may vary the parameters of the respective stimulation signal applied on each of the implanted electrodes. The patient may rate the effectiveness in pain reduction for each variation in the parameters of the stimulation signals. Then during chronic stimulation if electrical stimulation of nerve tissue does result in sufficient pain reduction for the patient, then the medical lead is implanted for the long term with stimulation signals having parameters that lead to optimized pain reduction for the particular patient.

Although spinal stimulation has proven effective for pain relief, there are problems associated with it, especially stimulation in the high cervical region. The conduit providing passage of the spinal cord in the lumbar vertebra provides more room for the spinal cord when compared to the conduit for the spinal cord in the cervical vertebra. In the lumbar region the spinal cord has a smaller diameter and therefore there is more room within the conduit of the lumbar vertebrae. As the spinal cord traverses up through the lumbar region of the spine to the cervical region, more and more peripheral nerves come into the spinal cord at the dorsal roots and therefore there is less room within. This poses a significant problem when placing the stimulation leads since the space in which to place the leads is diminished substantially.

Presently there are two basic styles of implantable leads available. One style is the percutaneously inserted lead, which is introduced through a Touhy needle. The implanting physician places the lead stimulating electrodes in an appropriate location using fluoroscopic visualization and the procedure is done under a local anesthetic. An example of this type of lead is disclosed in U.S. Pat. No. 4,379,462 issued to Borkan. Percutaneously inserted leads can be used for pain reduction/elimination, however, there are problems associated with these leads.

Percutaneously inserted leads are difficult to anchor and have a tendency to become dislodged. Even if the initial placement is accurate, lead migration can occur which can adversely affect paresthesia. Further, if the percutaneously inserted lead migrates enough to touch an incoming dorsal root, this can be very painful for the patient. Additionally, the area in which the patient is experiencing pain can move. This is a significant problem since percutaneous leads provide only limited means to change the area of stimulation if the lead migrates or if the needs of the patient change. Such means include reconfiguring the electrodes providing stimulation or performing additional surgery to adjust the lead's position. This problem could be resolved by enlarging the electrodes to cover more spinal cord area, however, the electrodes must be made small enough to fit through a Touhy needle. Thus, the stimulation area for percutaneous leads remains consequently small and because of this even a slight movement of the lead, especially laterally, can adversely affect paresthesia.

Another possible problem with percutaneous leads is their thickness is relatively large in comparison with the thickness of the dura mater in the high cervical region. Presently percutaneous leads are typically 0.050 inches in diameter. Because of the limited space in the high cervical region, if the lead is inserted improperly or if the lead migrates when placed in the cervical region where the dura mater is very thin, the percutaneous lead could possibly cause compression of the dura mater into the spinal cord causing discomfort, excess pain, and even paralysis.

The second basic spinal cord stimulation lead type is commonly referred to as a surgical lead and is surgically implanted in a procedure referred to as a laminotomy. An example of this type of lead is the RESUME® lead manufactured by Medtronic, Inc. of Minneapolis, Minn., the assignee of the present invention. This lead has four in-line electrodes located on a flat rectangular paddle at the distal end of the lead and the lead is normally implanted outside of the dura mater. Since leads of this type are surgically implanted, the size of the electrodes may be made larger than those of the percutaneously implanted leads. Further, various electrode combinations can be selected so that the area of stimulation may be moved along the midline of the spinal cord. The surgical lead can provide a broader stimulation pattern more suitable for midline and bilateral pain problems than the percutaneously inserted lead. Moreover, since it is surgically implanted it can be sutured to try and prevent dislodgement and reduce lead migration.

Surgical leads are less affected by the problem of lead migration because of the shape and size of the paddle and sutures may stabilize the lead. However, presently the paddles are made of silicon rubber, which requires a thickness of approximately 0.070 inches. Current technology does not allow the manufacture of desirably thin silicone rubber paddles suitable for locations with small extradural spaces such as the high cervical region due to production tolerances, coverage specifications, and internal anti-stretch components, which must be added to make the lead less elastic. Further, thin rubber coverage on silicon rubber paddles over internal components; such as the electrodes, are known to lack durability. Since the physician is trying to fit a rectangular lead into a cylindrical passage there is the potential for compression of the dura mater on the spinal cord. Therefore, inserting this rectangular lead still risks compression of the dura mater into the spinal cord causing discomfort, excess pain, and even paralysis.

Therefore, what is clearly needed is a method and apparatus for lead implantation in the high cervical region, which provides both improved fixation to prevent migration and an improved paddle structure to prevent compression of the dura mater against the spinal cord. What is further needed is a method for producing a thin paddle lead having improved fixation for implantation in the high cervical region.

SUMMARY OF THE INVENTION

The present invention provides for an implantable medical lead for electrical stimulation. The medical lead is comprised of a paddle. The paddle having at least one electrode electrically connected to at least one conductor with the paddle supporting the electrodes. The paddle having a thickness of up to 0.030 inches for application to small areas within the human body.

In another embodiment of the present invention, the medical lead is comprised of a paddle. A first paddle portion having a cavity on the surface of the first paddle portion and a second paddle portion having at least one aperture. There is at least one electrode electrically connected to at least one conductor. The at least one electrode is placed in the cavity of the first paddle portion and is disposed between the fist paddle portion the second paddle portion. The at least one electrode is disposed in such a way that a portion of the electrodes is conductively exposed through the at least one aperture.

In another embodiment of the present invention, an implantable medical lead for electrical stimulation comprises curved paddle portions having a distal and proximal end. On the surface of a first paddle portion there is a cavity and on the proximal end there is an opening extending from the proximal end of the first paddle portion to the cavity. The cavity is able to receive a second paddle portion having a plurality of apertures. The cavity contains a plurality of electrodes disposed between the first paddle portion and the second paddle portion with a conductive surface of each electrode at least partially exposed through the plurality of apertures. A plurality of conductors extending through the opening from the proximal end to the cavity is electrically connected to at least one conductor.

Another aspect of the present invention provides for a method of treating a medical condition using electrical stimulation. A paddle having at least one electrode and a thickness up to 0.030 inches is implanted adjacent a spinal cord dura in the cervical region of the spinal column. The paddle is then positioned so that at least one electrode is positioned over an area of the spinal cord for which electrical stimulation is anticipated to provide at least partial relief from a medical condition. Electrical stimulation is then applied to at least one electrode to provide at least partial relief from the medical condition.

Another aspect of the present invention provides a method of manufacturing an implantable medical paddle lead for electrical stimulation. A first paddle portion is created having a cavity on one side and an inlet for receiving at least one conductor. A second paddle portion is created having at least one aperture. At least one electrode located in the cavity is connected to at least one conductor. The second paddle portion is then placed onto the first paddle portion so that at least one electrode is positioned between the first paddle portion and the second paddle portion and a portion of at least one electrode is conductively exposed through the at least one aperture. The second paddle portion is then connected to the first paddle portion so that the medical lead has a thickness up to 0.030 inches.

DETAILED DESCRIPTION

To assist in an understanding of the invention, a preferred embodiment or embodiments will now be described in detail. Reference will be frequently taken to the figures, which are summarized above. Reference numerals will be used to indicate certain parts and locations in the figures. The same reference numerals will be used to indicate the same parts or locations throughout the figures unless otherwise indicated.

The present invention is not limited to only high cervical implantation or spinal stimulation leads, and may be employed in many of various types of therapeutic or diagnostic devices including spinal cord, peripheral nerve, deep brain, and deep brain stem stimulation leads. It is to be further understood, moreover, the present invention may be employed in many of various types of therapeutic or diagnostic leads and is not limited only to the high cervical leads. For purposes of illustration only, however, the present invention is below described in the context of high cervical implantation leads.

Figure 1:
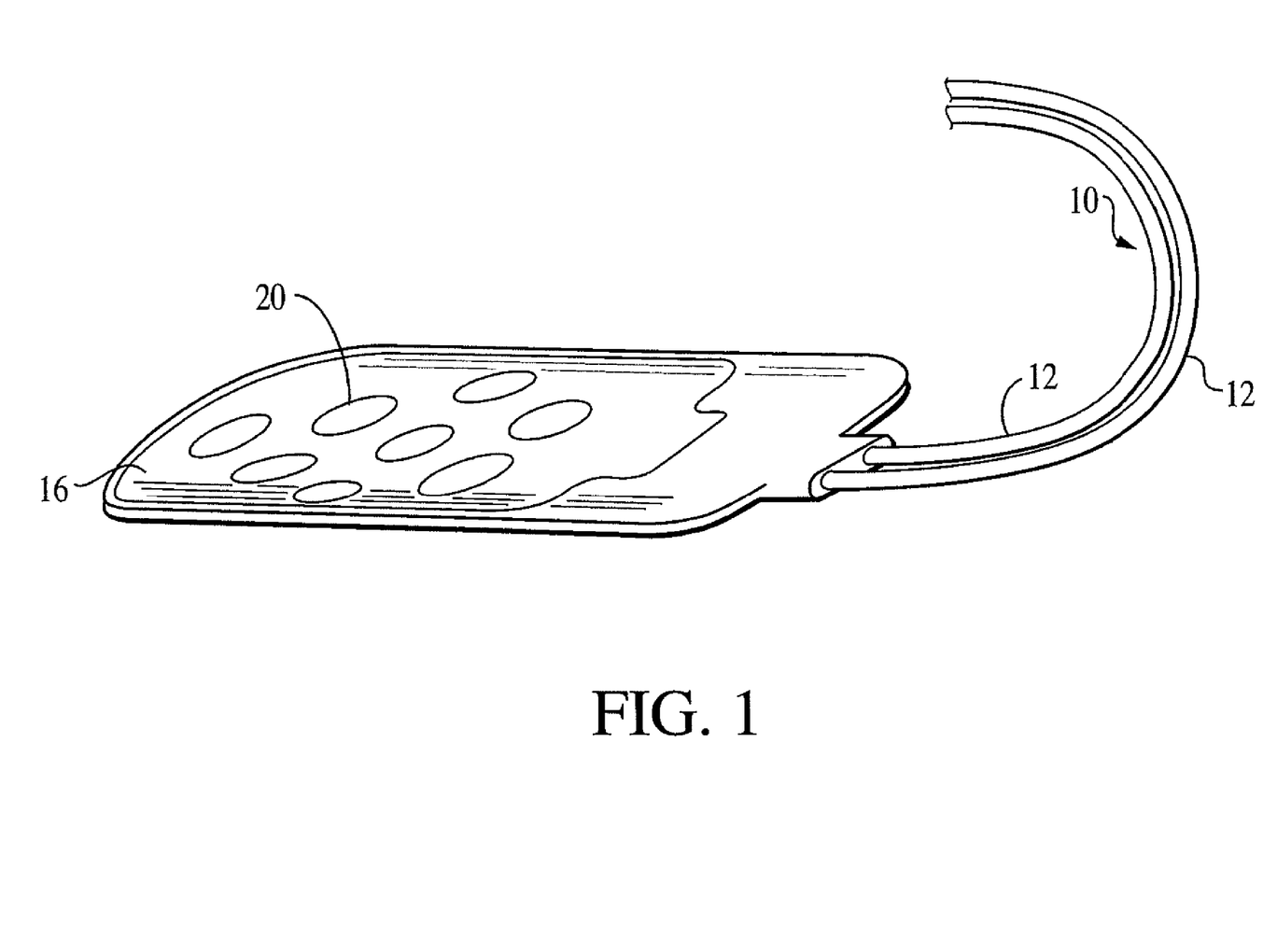
FIG. 1 is a plan view of one embodiment of the surgical lead of the present invention.

FIG. 1 is a plan view of one embodiment of a surgical lead of the present invention. Surgical lead 10 includes a pair of lead bodies 12 connected at their proximal end to a connector (not shown) of a type known in the art and at its distal end to a paddle 16. Lead bodies 12 can be made of any physiologically inert material such as silicone rubber or polyethylene; however, lead bodies 12 are preferable made of polyurethane so as to be compatible with paddle 16. Lead bodies 12 have lumens, which enclose at least one conductor 18 (FIG. 3) and most preferably have a diameter of 0.050 inches. Conductor 18 interconnects at least one electrode 20 located within paddle 16

Figure 2:
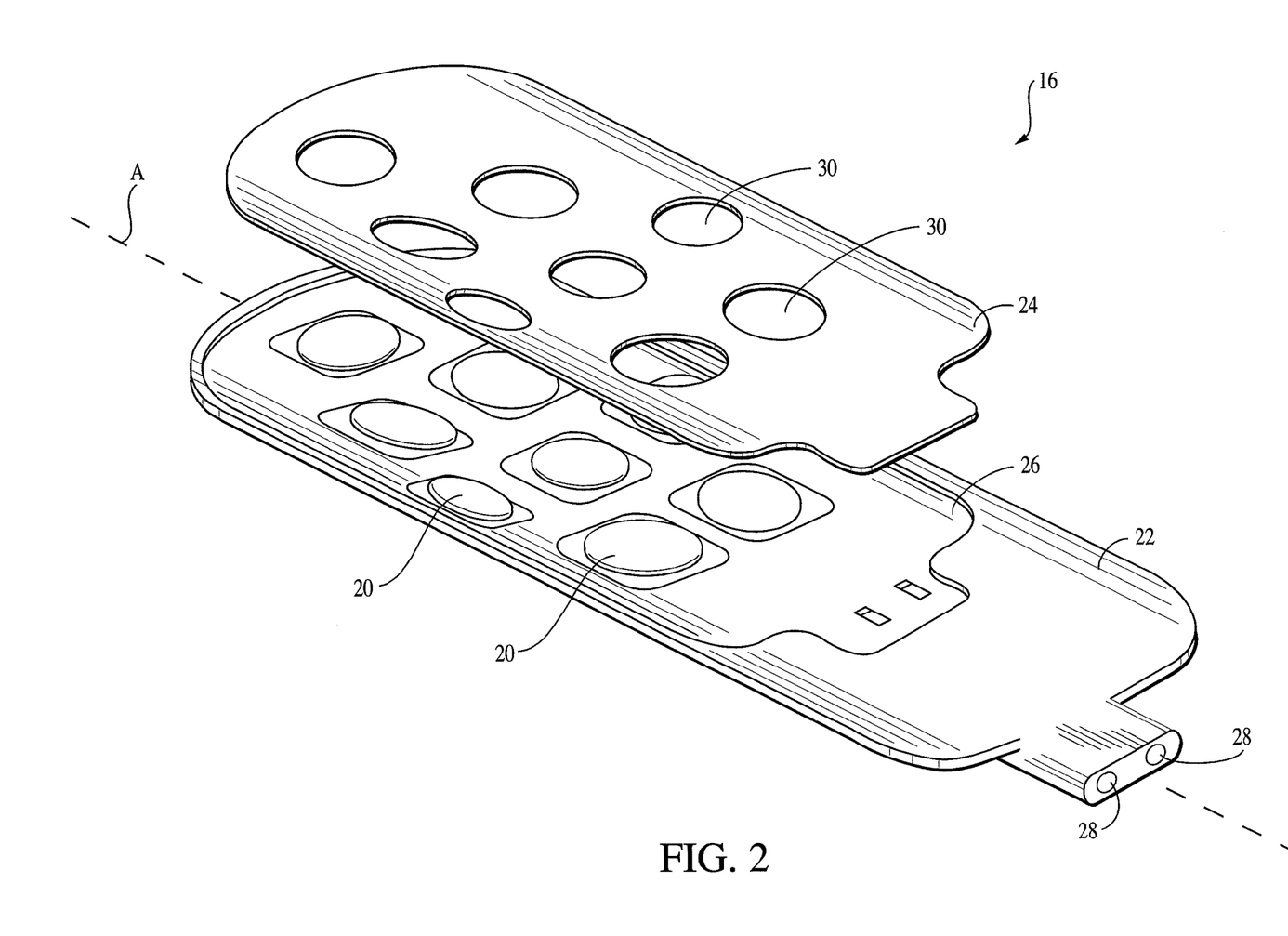
FIG. 2 is an exploded top side view illustrating an improved surgical lead of the present invention.

Referring to FIG. 2, an exemplary embodiment of a paddle 16 for spinal cord, peripheral nerve, deep brain, and brain stem stimulation of the present invention is shown. Paddle 16 comprises a first paddle portion 22 and a second paddle portion 24. First paddle portion 22 is further comprised of a cavity 26 and apertures 28 to accept at least one lead body 12.

Second paddle portion 24 has substantially the same shape as cavity 26 and is further comprised of openings 30. Cavity 26 is able to receive electrodes 20 within, which are electrically connected to conductors 18.

Paddle 16 is preferably comprised of molded transparent polyurethane and has a thickness no greater than 0.030 inches. Thickness is defined as the measurement taken from the bottom surface of paddle 16 to the top surface of paddle 16. Due to the paddle's polyurethane construction paddle 16 is more durable than any other physiologically inert material such as silicone rubber or polyethylene. Further, paddle 16 has better coverage specifications such as reduced coverage requirements over encapsulated components due to the durability of polyurethane and does not require any extra internal components, such as anti-stretch devices, which can significantly add to the paddle's 16 thickness. It is contemplated that as technology in molding part tolerances and durability advances it may be possible to use other physiologically inert materials such as silicone rubber or polyethylene in the present invention and therefore their eventual use is contemplated.

As can be seen from FIG. 2, paddle 16 is curved about axial line A. The curvature in paddle 16 is substantially similar to the natural curvature of the dura mater over the spinal cord. Further, the flexibility of polyurethane allows paddle 16 to easily form around the dura mater of the spinal cord depending on whether paddle 16 is implanted outside or inside of the dura mater. The size and curvature of paddle 16 eliminates any excess pressure on the dura mater or the spinal cord. First, the paddle's thickness allows for ease of implantation with reduced risk of spinal compression. Second, the base member's curvature eliminates excess spinal compression exhibited by inflexible rectangular paddle leads.

First paddle portion 22 of the present invention has a plurality of electrodes 20 arrayed along the length and across the width of first paddle portion 22 specifically within cavity 26. Varieties of alternate arrays and numbers of electrodes are contemplated. Paddle 16 with the array of electrodes 20 transmits stimulation signals to surrounding human tissue. The implantable pulse generator (FIG. 5) provides respective stimulation signals having specified signal parameters to selected electrodes 20 in the array. Thus, depending on the desired location and amount of tissue stimulation needed, the parameters of the stimulation signals can be controlled and directed to selected electrode contacts for targeted stimulation. Typically, for spinal cord stimulation, paddle 16 is placed outside the dura mater and stimulation occurs through the dura mater to the targeted tissue fibers within the spinal cord.

Figure 2A:
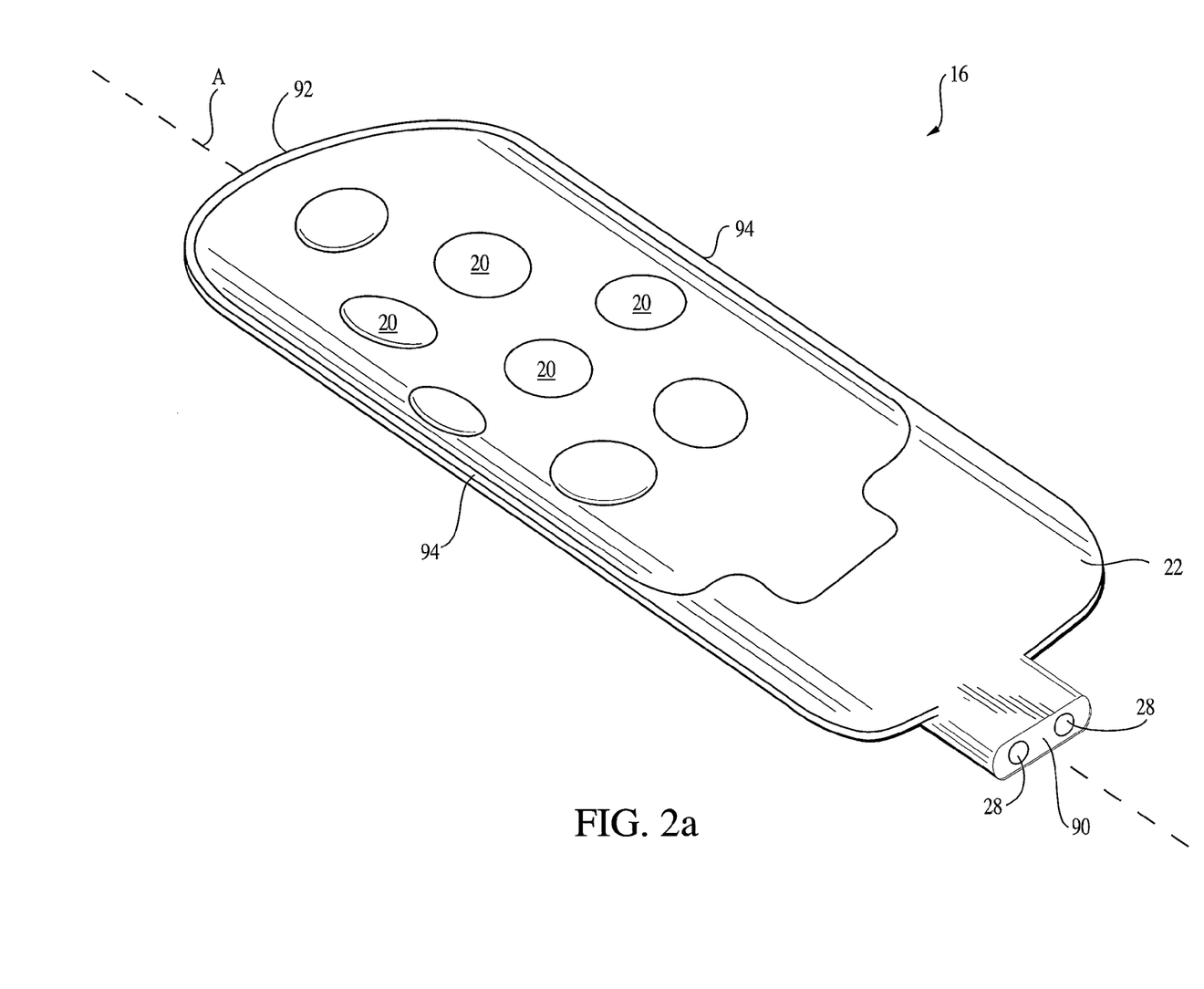
FIG. 2a is a top side view illustrating an improved surgical lead of the present invention.

Referring to FIG. 2a, as most preferred, paddle 16 has an array of eight electrodes 20 spaced axially along the length of first paddle portion 22 and laterally across the width. Electrode 20 sets upon first paddle portion 22 and protrudes slightly above the surface of plate body 24 in order to enhance tissue stimulation effectiveness. It is contemplated however, that electrode 20 can be recessed below the surface of second paddle portion 24. The array of electrodes 20 spans distant stimulation points, for example, nerve fibers, and at the same time provides combinations that cover stimulation points that may be close together. Because the epidural space restricts the width of any implanted body, the array of the present invention must span distant stimulation points to maximize the number of nerve fibers that are stimulated through the array. A clinician may direct stimulation to various combinations of stimulation points covered by the array of the present invention by controlling the amount and frequency to each electrode 20.

With reference again to FIG. 2a, a preferred paddle of the present invention is shown. In a preferred embodiment, first paddle portion 22 and second paddle portion 24 are fused together by injecting a volatile polyurethane adhesive inside of cavity 26. After injecting the volatile polyurethane adhesive into cavity 26, second paddle portion 24 is placed in cavity 26 with openings 30 accepting electrodes 20 within. The volatile polyurethane adhesive then begins to break down the polyurethane material of first paddle portion 22 and second paddle portion 24. As the surfaces of cavity 26 and second paddle portion 24 begin to break down or liquefy, the polyurethane structures begin to run together and fuse. Thus, there is no longer two independent bodies, but only one paddle 16.

Paddle 16 has a proximal end 90 and a distal end 92. Proximal end 90 provides openings 28 to accept at least one of the lead bodies 12 carrying conductors 18 into first paddle portion 22 and coupling to electrodes 20, which is discussed in more detail below. The distal end 92 is rounded and curved to prevent abrasion of human tissue for safer placement of the lead paddle at the desired stimulation area. The sides 94 of the paddle lead 16 are also rounded to prevent abrasion of tissue during implantation and while implanted. As discussed above, paddle 16 is curved laterally to match the curvature of the spinal cord dura mater. Curved paddle 16 enhances the likelihood of fiber stimulation by allowing electrodes 20 to be in close proximity to the targeted tissue fibers thus improving fiber recruitment. Moreover, as discussed above, a curved paddle 16 reduces the potential for compression of the spinal cord.

Figure 3:
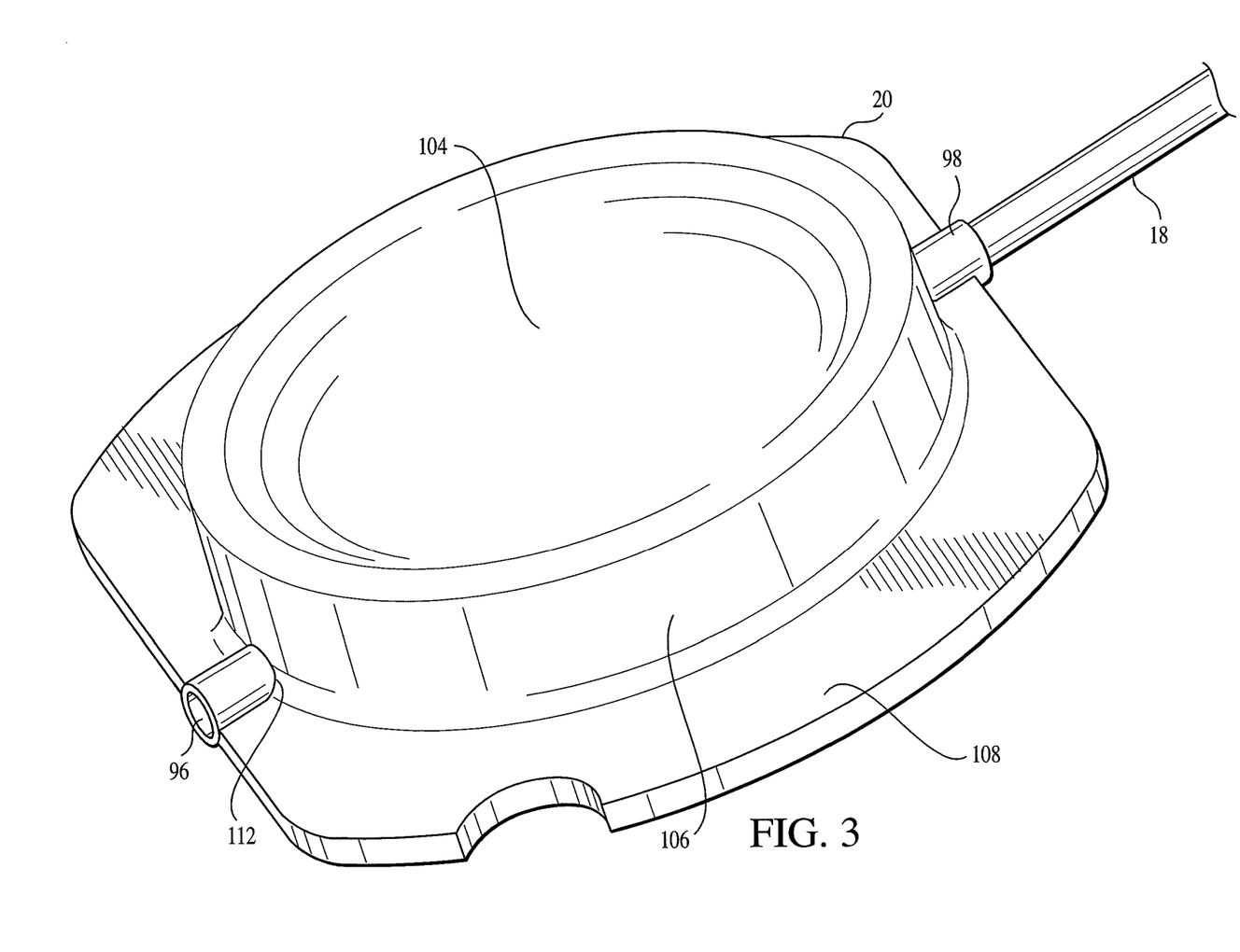
FIG. 3 is a top side view of an embodiment of an improved connection between a conductor and an electrode.
Figure 4:
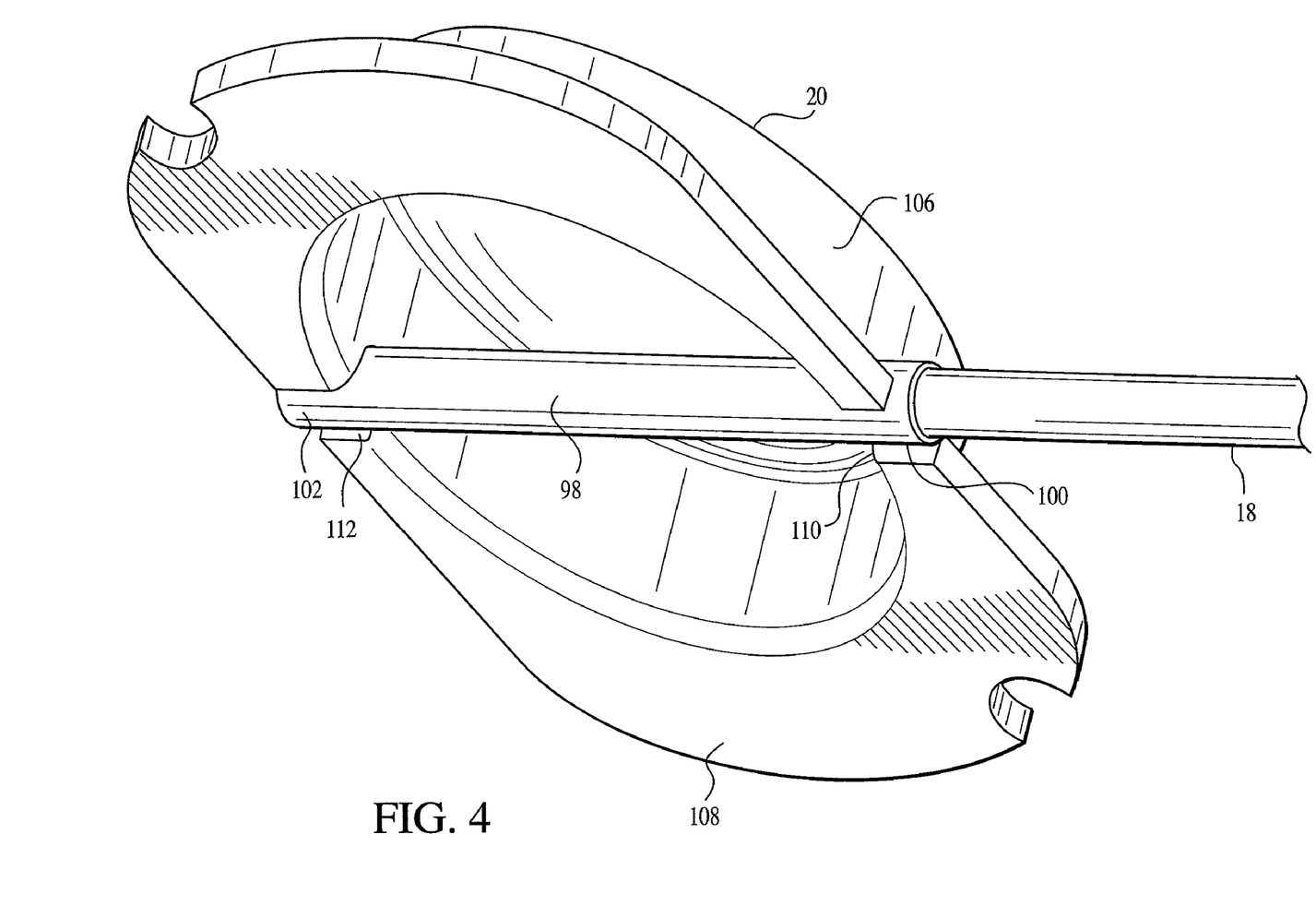
FIG. 4 is a bottom side view of an embodiment of an improved connection between a conductor and an electrode.

With reference to FIGS. 3 & 4, a preferred embodiment of an improved connection between conductor 18 and electrode 20 is shown. Conductor 18 is contained in lead body 12 and generally extends from the connector (not shown) to paddle 16. Conductor 18 can be manufactured from a wide range of materials that are electrically conductive such as nickel-titanium, platinum, gold, silver, palladium, other noble metals, and other alloys or metals suitable for use in the human body. However, in a preferred embodiment low impedance is desired. Therefore, the core of each conductor is manufactured from low impedance metal such as silver and the jacket is manufactured from a material with good mechanical strength properties such as MP35N. Conductor 18 preferably has a resistance of less than 10/ohms/cm (3 ohms/foot) and a tensile strength greater than 5N, however, other resistances and tensile strengths are contemplated. Further, conductor 18 preferably is electrically insulated with a flouro-polymer such as ethyletetraflouroethylene or polytetrafluoroethylene (PTFE) with a coating thickness of approximately 0.0005 inch. In a preferred embodiment conductor 18 comprises a plurality of wires configured as braided strand wire (BSW) and is capable of reliably conducting electrical current after having been subjected to numerous, repeated bending and torquing stresses. BSW is available in many configurations including seven wire BSW. Three wires, however, have been discovered to provide the best overall combination of maximum strength, minimum diameter, and maximum torque transfer between proximal and distal ends. Each wire preferably has a diameter of between about 0.002 and about 0.006 inches, and most preferably has a diameter of about 0.004 inches. The number of conductors may be increased to two, three, or more, dependent on need and generally to the number of electrical signals to be generated. The term "about" applies to all numeric values, whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Electrodes 20 are preferably formed of a non-corrosive, highly conductive material. Examples of such material include platinum and platinum alloys. In a preferred embodiment, electrodes 20 are formed of a platinum-iridium alloy. As can be seen in FIGS. 3 & 4, electrode 20 has a hat-like structure with top surface 104, an annular side surface 106, a base 108, and arches 110 & 112 which receive conduit 96 as discussed in more detail below. It is contemplated that electrode 20 can take on many structures including a flat structure as long as the structure is able to be held between first paddle portion and second paddle portion. Top surface 104 provides electrical contact with the tissue to be stimulated and preferably extends slightly beyond second paddle portion 24 as discussed above. Top surface 104 is also recessed to accommodate the dura mater of the spinal cord and thus further reduce any compression of the dura mater. Base 108 secures electrode 20 in-between first paddle portion 22 and second paddle portion 24. When first paddle portion 22 and second paddle portion 24 are attached as discussed above, base 108 is placed between the two and thus prevents electrode 20 from being easily dislodged. In a preferred embodiment, and based on past studies to reduce the potential of lesions from smaller contact areas, the size of electrodes 20 is preferably approximately 3 square millimeters. However, electrode contacts of other suitable sizes are contemplated and within the scope of this invention.

In a preferred embodiment, conductor 18 is electrically attached to electrode 20 in a way, which provides improved strain relief. At the distal end of conductor 18 a portion of the conductor's coating is removed in preparation for attachment to electrode 20. Conductor 18 is then inserted approximately halfway through conduit 96 of crimp sleeve 98. By inserting conductor 18 approximately halfway through conduit 96 silver ion migration is mitigated. Previous connections connected the conductor directly to the electrode and if the conductor were comprised of silver the silver ions would pit or deteriorate the weld joint between the conductor and the electrode. This increased the chances of conductor separation and silver exposure to patient tissue. Next, crimp sleeve 98 is crimped to create a stable electrical attachment. Since, silver material is not ideal for forming a strong mechanical connection crimp sleeve 98 is also used provide a strong mechanical connection between conductor 18 and electrode 20. Crimp sleeve 98 is then laser welded to electrode 20 at arches 110 & 112 located at proximal end 100 and distal end 102 respectively. Therefore, the improved connection between electrode 20 and conductor 18 provides an improved mechanical connection as well as a reduction in silver ion migration.

Figure 5:
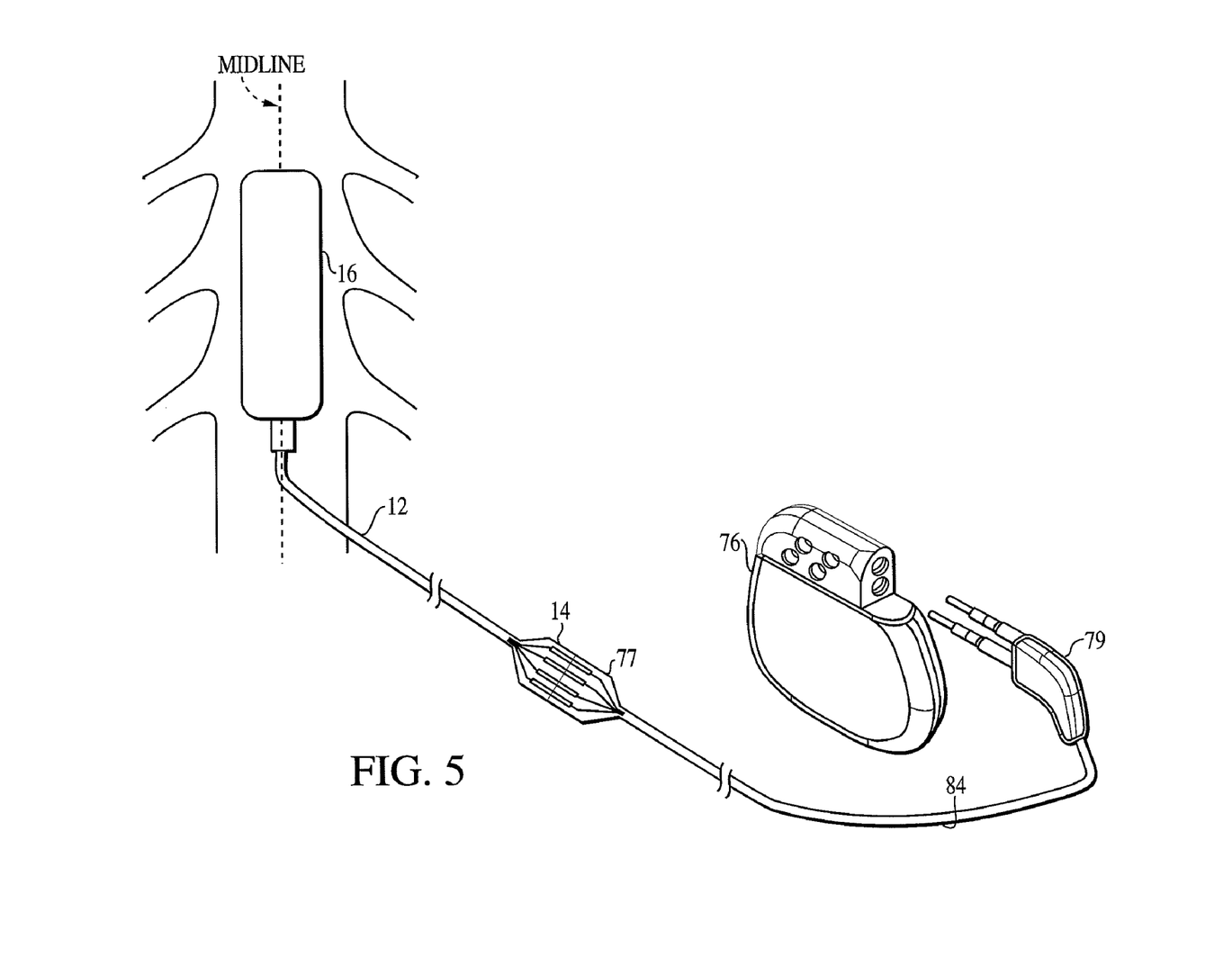
FIG. 5 is a partial schematic view of the spinal cord of a patient with the implanted surgical lead paddle of FIG. 2 connected to a pulse generator.
Figure 6:
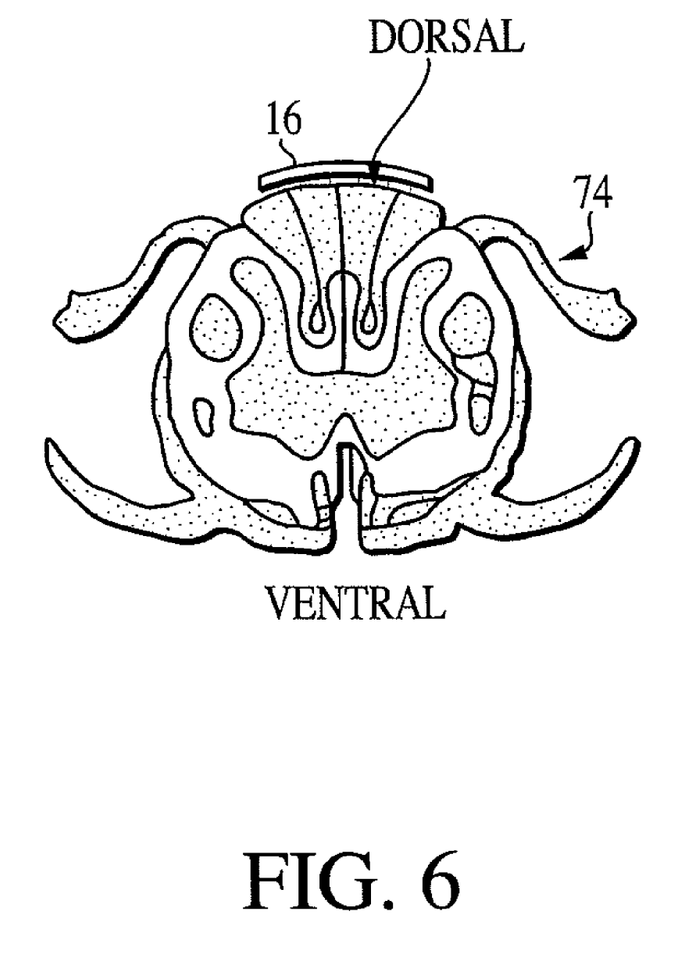
FIG. 6 is a cross sectional view schematically illustrating the spinal column of a patient with the base member of FIG. 2 positioned on the dorsal side thereof.

As shown in FIGS. 5 & 6, paddle 16 is adapted to be implanted in a human patient along the dorsal side of the spinal column 74. As best seen in FIG. 5, typically the lead is implanted over the midline of the spinal cord. If more than one electrode 20 is used than each electrode can be independently selectable so that when paddle 16 is positioned as shown a variety of stimulation patterns may be selected by providing stimulation signals to two or more of electrodes 20. An external pulse generator provides the stimulation signals or pulses during the screening procedure. After the initial electrode combination is selected, the lead is connected to an implanted pulse generator 76 by a lead extension 84. Lead extension 84 has a connector 77 at its distal end, which connects to connector 14 and has a plug-in connector 79 at its proximal end, which connects to pulse generator 76. Pulse generator 76 may be a fully implanted system such as the "ITREL I1" pulse generator available from Medtronic Inc.

In use, paddle 16 is designed to be implanted in the high cervical space where the space between the vertebrae and dura mater is very thin after the dura has been exposed by a partial laminectomy. As can be appreciated the base member's reduced thickness and curved structure not only improve electrical stimulation capabilities, but also reduce the risk of spinal cord compression by allowing paddle 16 to move with the spinal environment in contrast to the flat paddle being so tightly inserted that it causes compression during movement. Although the invention will be described primarily in connection with its implantation in the high cervical space along the dorsal column for use in stimulating the spinal cord as a method of treating pain, it should be noted that paddle 16 could be used for any spinal cord stimulation application such as stimulation to induce motor function or to inhibit spasticity. When used for such other applications the lead could be implanted laterally or on the ventral side of the spinal column. The lead is also suitable for use in applications other than spinal cord stimulation such as stimulation of peripheral nerves.

As discussed above, once the lead has been implanted a screening procedure is performed to determine if the position of the lead will adequately supply paresthesia to the desired location. During the screening process, various electrode combinations are tested until the right combination is achieved. By using the lead of the present invention various unilateral and/or bilateral stimulation combinations are possible.

After the screening process is completed and the lead is properly anchored in place the lead is disconnected from the external screening device and connected to the implanted pulse generator so that the entire system can be internalized. Once the stimulation system has been internalized the lead of the present invention provides the flexibility to make modifications to the area of paresthesia should the needs of the patient change or should there be any lead migration. This is done by changing the electrode combinations by external programming procedures well known in the art. Thus, the need for repositioning or removing the lead is greatly reduced.

Thus, embodiments of the Improved Surgical Lead Paddle for High Cervical Implantation are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of making an implantable medical lead for electrical stimulation, comprising:
    forming a paddle, comprising;
        a first paddle element having a recessed cavity formed on one side of the first paddle element;
        a second paddle element having at least one aperture, wherein the second paddle element is received by the cavity of the first paddle element; and
        at least one electrode electrically connected to at least one conductor, said at least one electrode being disposed between the first paddle element and the second paddle element with a portion of the at least one electrode being conductively exposed through the at least one aperture.

2. The method of making an implantable medical lead of claim 1, wherein the second paddle portion has substantially the same shape as the cavity of the first paddle portion.

3. The method of claim 1, wherein the paddle has a thickness for application to a human spinal cord.

4. The method of claim 3, wherein the paddle is configured to be applied to cervical vertebrae in the human spinal cord.

5. The method of claim 3, wherein said paddle is configured to be applied to lumbar vertebrae in the human spinal cord.

6. The method of claim 1, wherein the first and second paddle element have a combined thickness up to .030 inches for application to small areas within the human body.

7. The method of claim 1, wherein the first and second paddle elements are curved along a vertical axis.

8. The method of claim 7, wherein the curved paddle elements are substantially similar to the shape of a human spinal cord.

9. The method of claim 1, wherein said first and second paddle elements have a combined thickness up to .025 inches.

10. The method of claim 1, wherein said first and second paddle elements have a combined thickness up to .020 inches.

11. A method of making an implantable medical lead for electrical stimulation, comprising:

forming a paddle, comprising;
    a first paddle element having a recessed cavity formed on one side of the first paddle element;
    a second paddle element with an aperture, the second paddle element having substantially the same shape as the cavity of the first paddle element, wherein the second paddle element is received in the cavity of the first paddle element; and
    an electrode electrically connected to a conductor, said electrode being disposed between the first paddle element and the second paddle element wherein the electrode is conductively exposed through the aperture.

12. The method of making an implantable medical lead of claim 11, wherein the second paddle portion has substantially the same shape as the cavity of the first paddle portion.

13. The method of claim 11, wherein the paddle is curved along a vertical axis.

14. The method of claim 13, wherein the curved paddle is substantially similar to the shape of a human spinal cord.

15. The method of claim 11, wherein the paddle has a thickness up to .025 inches.

16. The method of claim 11, wherein the paddle has a thickness up to .020 inches.

17. The method of claim 11, wherein the paddle has a thickness configured for application to a human spinal cord.

18. The method of claim 11, wherein the paddle is configured for application to cervical vertebrae in a human spinal cord.

19. The method of claim 11, wherein the paddle is configured for application to lumbar vertebrae in a human spinal cord.

* * * * *